United States Patent [19]
Kell

[11] Patent Number: 5,602,038

[45] Date of Patent: *Feb. 11, 1997

[54] METHOD OF DETERMINING RENAL CLEARANCES

[75] Inventor: Michael Kell, Atlanta, Ga.

[73] Assignee: Private Clinic Laboratories, Inc., Atlanta, Ga.

[*] Notice: The term of this patent shall not extend beyond the expiration date of Pat. No. 5,500,372.

[21] Appl. No.: 591,406

[22] Filed: Jan. 25, 1996

Related U.S. Application Data

[63] Continuation-in-part of Ser. No. 279,400, Jul. 25, 1994, Pat. No. 5,500,372.

[51] Int. Cl.$^6$ .................................................. G01N 33/50
[52] U.S. Cl. .................................................. 436/98
[58] Field of Search ........................... 436/63, 98, 174, 436/811

[56] References Cited

U.S. PATENT DOCUMENTS

| | | | |
|---|---|---|---|
| 4,529,708 | 7/1985 | Stephens | 436/98 |
| 4,818,703 | 4/1989 | Pizzolante | 436/98 |
| 5,500,372 | 3/1996 | Kell | 436/98 |

OTHER PUBLICATIONS

Robertshaw, M. "Prediction of Creatinine Clearance from Plasma Creatinine: Comparison of Five Formulae" Br. J. Clin. Pharmac., vol. 28, 275–280 (1989).

Rosano, J. G. et al. "Analytical and Biological Variability of Serum Creantinine and Creatinine Clearance" Clinical Chemistry, vol. 28, 2330–2331 (1982).

Gowans, E. et al. "Biological Variation of Serum and Urine Creatinine and Creatinine Clearance" Chemical Abstracts, vol. 109, No. 356603v, (1988).

Konishi, K. et al. "Prediction of Creatinine Clearance from the Serum Creatinine Clearance" Chemical Abstracts, vol. 102, No. 2885r (1985).

*Primary Examiner*—Jeffrey Snay
*Attorney, Agent, or Firm*—Kennedy & Kennedy

[57] ABSTRACT

In a method of determining creatinine clearance for detecting and monitoring renal dysfunction, spot samples of urine and blood from a person are obtained. Specific gravity or osmolality and creatinine concentration of the urine sample are measured. Creatinine concentration of plasma of the blood sample is also measured. Creatinine clearance is calculated as a function of the measured urine specific gravity or osmolality, the measured urine creatinine concentration and the measured plasma creatinine concentration.

6 Claims, 7 Drawing Sheets

URINE SPECIFIC GRAVITY FACTOR (1.03-1/SG-1)

METHOD OF DETERMINING RENAL CLEARANCES

REFERENCE TO RELATED APPLICATION

This application is a continuation-in-part of application Ser. No. 08/279,400 filed Jul. 25, 1994 now U.S. Pat. No. 5,500,372.

TECHNICAL FIELD

This invention relates to methods of detecting and monitoring the progression of renal dysfunction. More particularly, the invention relates to methods of screening medical patients for occult renal dysfunction.

BACKGROUND OF THE INVENTION

In the fields of medicine and physiology, an accurate assessment of renal function is essential for diagnosis and evaluation of the progression of acute and chronic injuries to the kidneys. During the course of chronic renal disease, the rate of loss of renal function is generally constant. Decreasing function has been shown to occur because of damage to the individual filtration units of each kidney, known as nephrons. Each kidney has approximately $10^6$ nephrons.

In developing the prognosis and therapy for patients with chronic renal failure (CRF), the residual value of a glomerular filtration rate (GFR) is typically used. The GFR represents the sum total volume of whole blood filtrate which is processed by the glomeruli of both kidneys. For a healthy adult the GFR typically ranges from 120 to 125 ml/min filtered.

Several methods are used to estimate GFR under standard conditions. One method utilizes an intravenous infusion of inulin to measure inulin clearance as an estimate of GFR. The inulin must be carefully regulated to maintain a constant plasma concentration of drug while a timed urine sample is collected, usually over a 24-hour period. Timed urine sample collection is typically inaccurate due to daily variations in urine flow, incomplete emptying of the bladder, and partial loss of the sample. Under optimal conditions, the coefficient of variation (CV) for inulin clearance as compared to GFR is approximately 10 percent in healthy patients and higher in patients with CRF or other severe illnesses.

Another method for estimating GFR employs various radiolabled compounds that are eliminated by glomerular filtration only. Most of these compounds are gamma-emitters, thereby avoiding the error caused by variable quenching in plasma and urine samples as occurs with beta-emitters. While this method is easier to use than the inulin method, and has similar CV (10–17 percent), it presents radiation-safety hazards and many practical handling considerations.

Due to the difficulties inherent in the above methods for estimating GFR, clinicians have relied instead upon measuring creatinine clearances. Creatinine, a waste product of muscle metabolism, is a metabolic side-product occurring in parallel to phosphorocreatine metabolism. Phosphorocreatine is produced from creatine. Creatine is manufactured in the liver from glycine and arginine, transferred to skeletal muscle and converted to the energy-rich compound phosphorocreatine. As creatine cycles between itself and phosphorocreatine in muscle, a small amount of creatine is irreversibly converted to creatinine which is excreted through the kidneys.

The 24-hour creatinine clearance slightly exceeds inulin clearance due to tubular secretion of creatinine in the proximal tubules of each nephron. This method, while not requiring the introduction of an exogenous substance into the patient, does require venipuncture for a blood sample and timed urine sample collection. Consequently, this method is also highly susceptible to errors in timed urine sample collection as discussed above with regard to the inulin clearance method. Estimates for day-to-day variability in ambulatory patients are typically as high as 26 percent. Some portion of this variability is due to daily variations in creatinine metabolism, but the majority is due to urine collection difficulties.

Although estimates for GFR are easier with creatinine than inulin, such procedures are not amenable to routine patient screening due to the necessity of collecting a large volume of urine, usually over a 24 hour period. Consequently, patients are generally only screened for renal function after they develop physical symptoms ascribable to renal dysfunction. This oftentimes allows occult damage to occur that was potentially preventable.

Thus, there exists a need for a simplified method of routinely monitoring patients for renal dysfunction without the necessity for timed urine sample collections and employment of exogenous substances. Accordingly, it is to the provision of such an improved method that the present invention is primarily directed.

SUMMARY OF THE INVENTION

In a preferred form of the invention creatinine clearance is determined for detecting and monitoring renal dysfunction. Spot samples of urine and blood from a person are obtained. Specific gravity or osmolality of the urine sample is measured. Creatinine concentration of plasma of the blood sample and of the urine sample are measured. Creatinine clearance is then calculated as a function of the measured urine specific gravity or osmolality, the measured urine creatinine concentration and the measured plasma creatinine concentration.

DETAILED DESCRIPTION OF THE INVENTION

Figures 1, 2:
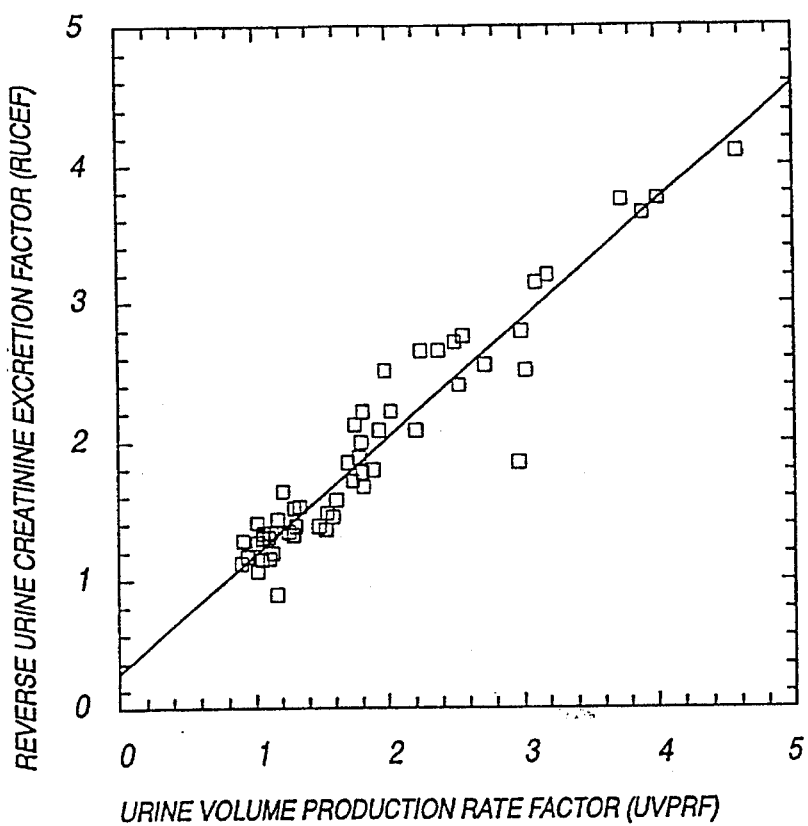
FIG. 1 is an empirically derived graph of reverse urine creatinine excretion factor (RUCEF) versus urine volume production rate factor (UVPRF) showing their linear relationship.
FIG. 2 is an empirically derived graph of urine volume production rate factor (UVPRF) versus specific gravity factor (SGF) showing their linear relationship.

Glomerular filtration rate is estimated by determining creatinine clearance using a new simplified method which does not require timed urine sample collection. Thus, physicians are now able to detect and monitor renal dysfunction during routine office visits. Spot samples of a person's urine and blood are obtained. The urine specific gravity at room temperature and the urine and blood plasma creatinine concentrations are determined. A specific gravity normalized creatinine concentration, nu, is calculated by adjusting the urine creatinine concentration for compounding effects of urine specific gravity. A relationship has been discovered to exist between nu and the plasma creatinine concentration such that an approximate value for creatinine clearance may be calculated and therefore GFR can be estimated. Alternatively, the urine osmolality is measured and used in the calculations in lieu of the specific gravity, inorder to overcome specific gravity measurement problems associated with urine samples having high protein or glucose concentrations.

Collection of Blood and Urine Samples

An aliquot of blood is collected using standard venipuncture techniques, though arterial samples may be used, if necessary. While the time of blood sampling does not have to be concurrent with that of urine sampling, accuracy is enhanced whenever both samples are collected simultaneously or at least within several hours of each other.

The urine sample is collected by simply providing the patient with a standard urine collection bottle into which he or she can urinate. Alternatively, a sample can be collected by catheterization or withdrawn from a urine collection bag. Only several milliliters of urine are required for analysis. With this sampling method, it is not necessary to record the volume collected or completely void the bladder. Loss of a portion of the sample is also not detrimental as long as a sufficient sample remains for analysis. Consequently, this new method overcomes problems long associated with attempts to collect timed urine samples as required by previous clinical methods.

Measurement of Specific Gravity or Osmolality and Creatinine Concentrations

Once a representative urine sample has been obtained, urine specific gravity is measured at room temperature, which typically ranges from 1,004 to 1,035 for normal urine. A Digital Urinometer by Biovation may be used for this test. Occasionally, urine samples may exhibit artificially elevated specific gravity values. This situation occurs whenever the urine contains a significant amount of protein, such as in the nephrotic syndrome, and/or glucose, as in diabetes mellitus. Occasionally, this can also occur when urinary cleared, radiopaque dyes are used for diagnostic purposes.

Osmolality measurement may therefore be preferred in lieu of specific gravity measurement in order to avoid these inflated values, since osmolality values are less dramatically affected by the presence of glucose and protein in the urine, and since there is a recognized relationship in scientific literature that exists between urine osmolality and urine specific gravity.

Creatinine concentrations for urine and plasma may be determined with any number of analyzers, including the REA Creatinine Analysis on the TDX System available from Abbott Laboratories and FARO Analyzers available from Roche Diagnostics. The creatinine concentration in human urine usually ranges from 8 to 500 mg/dl. The range is affected by variables such as age, sex, diet, lifestyle and geographic location. Plasma creatinine concentrations generally are homeostatically maintained by the body at a constant value for each individual patient over his or her lifetime. Daily generation of creatinine remains constant unless crushing injuries or degenerative diseases cause massive muscle damage. Reference values for plasma creatinine concentrations for healthy adult males average between 0.6 to 1.3 mg/dl; for females 0.5 to 1.0 mg/dl. While the illustrative method employs plasma creatinine concentrations, blood or serum creatinine concentrations may also be used.

Determination of the Specific Gravity Normalized Urine Creatinine Concentration

The parameters of a patient's urine, such as pH and specific gravity, vary from one day to the next dependent upon the type and quantities of foods and beverages ingested. Additionally, individuals metabolizes endogenous substances, as well as medications, at different rates. Due to variations in these daily urine parameters, concentration levels for creatinine and other endogenous compounds and drug metabolites can vary over time. Since many endogenous compounds and drugs are weak acids under normal conditions of urine pH, significant tubular resorption does not occur and renal clearance is primarily the result of glomerular filtration. For these compounds, the major variable responsible for observed variations in urine metabolite and drug concentrations is tubular resorption or excretion of free water. The kidneys regulate urine production rates so to maintain normal blood pressure and blood osmolality. This property of the kidneys is indicated by the urine specific gravity, a physical variable relating to urinary solids and urine volume production rate. A mathematical relationship has been discovered to exist between urine creatinine concentrations and urine specific gravity, which herein is given by the specific gravity normalized creatinine concentration, nu.

In order to determine the particular form to use for nu for creatinine or any other compound, it is now realized that renal excretion rates (mg/dl) for drugs and urine metabolites are relatively constant for any patient during a typical day. This constancy has now been experimentally verified by examining the renal excretion rates of methadone, benzodiazepines, other drugs and creatinine and other endogenous metabolites as a function of urine volume production rate. Sequential, complete and timed (1–8 hours holding periods) aliquots of urine for 12 compliant control subjects were collected over 24 to 72 hour periods. For each urine aliquot, urine volume production rate (ml/min), specific gravity and creatinine concentration (mg/dl) were determined. Using this data, a dimensionless, linear relationship was found to exist, that is the same for all patients, between a urine volume production rate factor (UVPRF) and a reverse urine creatinine excretion factor (RUCEF). For each individual, control, urine collection period, the UVPRF is defined by the ratio of urine volume production rate for each urine aliquot collected, v, to the urine volume production rate for the most concentrated sample in the collection period with a specific gravity usually near 1.030, v', $$UVPRF = v/v' \tag{1}$$

The RUCEF factor is defined by the ratio of the creatinine concentration of the most concentrated urine aliquot with a specific gravity usually near 1.030, u', to the creatinine concentration for each urine aliquot collected, u, $$RUCEF = u'/u \quad (2)$$

This linear relationship is shown in FIG. 1. The best fit linear regression line is given by the expression, $$RUCEF = 0.942 \cdot UVPRF + 0.121 \quad (3)$$

$$u'/u = 0.942 \cdot v/v' + 0.121 \quad (4)$$

where statistical evaluation results in an adjusted squared multiple R=0.985, a standard error of the estimate=0.242, and a F-ratio=4965.

Therefore, contrary to the traditional teachings of those skilled in the art, urine drug and metabolite concentrations, u, are inversely related to the volume of urine produced by the kidneys, v, clearly demonstrating that the product (u·v) is constant at any particular time point and urine pH.

Since (u·v) at any time is a constant, steady-state value, it follows that from Equation (4) some empirical mathematical relationship must exist between u and v such that given an arbitrary urine volume production rate v' and an equivalent u' at a reference point (specific gravity 1.030):

$$\{u \cdot v\}_{sg\ actual} = \{u' \cdot v'\}_{sg\ 1.030} \quad (5)$$

or upon rearrangement for u' gives, $$u' = u \cdot (v/v') \quad (6)$$

where the products given in Equation (6) are those measured for a spot urine collected with an actual specific gravity and a corrected specific gravity typical of a morning void of 1.030.

Using controlled urine collections, a urine volume production rate v' of 0.44 ml/min for persons with reasonably normal renal functions at a specific gravity of 1.030 was initially measured. It was discovered that a linear relationship exists between the urine volume production rate factor and the specific gravity factor (SGF), {(1,030- 1.000)/(sg - 1,000)}, as shown in FIG. 2 and given as follows:

$$UVPRF = v/v' = 2.43 \cdot SGF - 1.43 \quad (7)$$

where the adjusted squared multiple R=0.856, standard error of the estimate=0.787, F-ratio 482.

Substituting Equation (7) into Equation (6) the specific gravity normalized creatinine concentration, nu, is calculated by adjusting the actual urine creatinine concentration, u, for compounding effects of urine specific gravity.

$$nu = u' = u \cdot (v/v') = u \cdot [2.43 \cdot SGF - 1.43] \quad (8)$$

Calculation of Creatinine Clearance

The creatinine clearance is calculated by estimating three variables, the plasma creatinine concentration, the urine creatinine concentration and the volume of urine collected over a 24 hour collection period. Creatinine clearance is calculated utilizing the standard dimensionally correct relationship known as the renal clearance formula, which is:

$$cl = (u \cdot v)/p \quad (9)$$

where cl is renal clearance (ml/min), u is actual urine concentration (mg/dl), v is the volume of urine collected in time (ml/min) or otherwise known as the urine volume production rate, and p is the measured plasma concentration at the midpoint of the collection period (mg/dl). The plasma and actual urine creatinine concentrations are measurable as discussed above by using known chemical or other methods. However, under normal clinical screening situations the actual value of the urine volume production rate, v, is not available to physicians due to the great effort and expense required to obtain this value by collecting a timed urine sample for ambulatory patients during normal health check-ups.

By substituting Equations (5) and (8) into the renal clearance formula of Equation (9), the creatinine clearance is calculated in accordance with the invention as follows:

$$\begin{aligned} cl &= (v \cdot u)/p \quad (10) \\ &= (v' \cdot u')/p \\ &= v' \cdot u \cdot [2.43 \cdot SGF - 1.43]/p \end{aligned}$$

All the values of Equation (10) are readily available, v' is equal to 0.44 ml/min and u, p and urine specific gravity are obtainable using standard measurement techniques. The problem of obtaining urine volume production rate is now eliminated since a spot urine sample may now be collected rather than a timed urine sample in order to estimate GFR. There is no additional inconvenience for the patient since urine samples are often collected from patients for other reasons. Moreover, by evaluating sequential samples from an individual patient an accurate individual base value of creatinine clearance and GFR is obtained.

Biological Variation in Plasma/Urine Creatinine Concentrations

Based upon past literature references, some degree of biological variability was to be expected in repetitive measurements of urine and plasma creatinine concentrations. However, quantitative data actually available demonstrating variability was minimal. Thus, data relating to creatinine concentration variability was developed.

To evaluate daily variation in plasma creatinine concentration, morning and afternoon blood samples were drawn for 13 control subjects. Actual before noon (AM) and after noon (PM) plasma creatinine concentrations measured for each subject are shown in Table A, as well as the PM/AM ratio. Using the ratio data, the mean ratio was 1.02, a standard deviation (SD) of 0.12 and a CV of 11.6 %. A slightly elevated ratio was to be expected since plasma creatinine concentration is known to increase slightly with the ingestion of protein and with exercise.

TABLE A

Daily Variation in Plasma Creatinine

| Subject | AM Creatinine (mg/dl) | PM Creatinine (mg/dl) | PM/AM Creatinine Ratio |
|---|---|---|---|
| A | 1.11 | 1.18 | 1.063 |
| B | 1.14 | 1.17 | 1.114 |
| C | 1.27 | 1.06 | 0.835 |
| D | 0.81 | 0.67 | 0.827 |
| E | 1.4 | 1.53 | 1.093 |
| F | 0.91 | 1.06 | 1.165 |
| G | 0.85 | 1.01 | 1.188 |
| H | 1.30 | 1.27 | 0.977 |
| I | 1.34 | 1.45 | 1.082 |
| J | 0.90 | 0.79 | 0.878 |
| K | 1.20 | 1.25 | 1.042 |
| L | 1.20 | 1.23 | 1.025 |
| M | 1.20 | 1.15 | 0.958 |
| Mean | | | 1.02 |
| SD | | | 0.12 |

Figure 3:
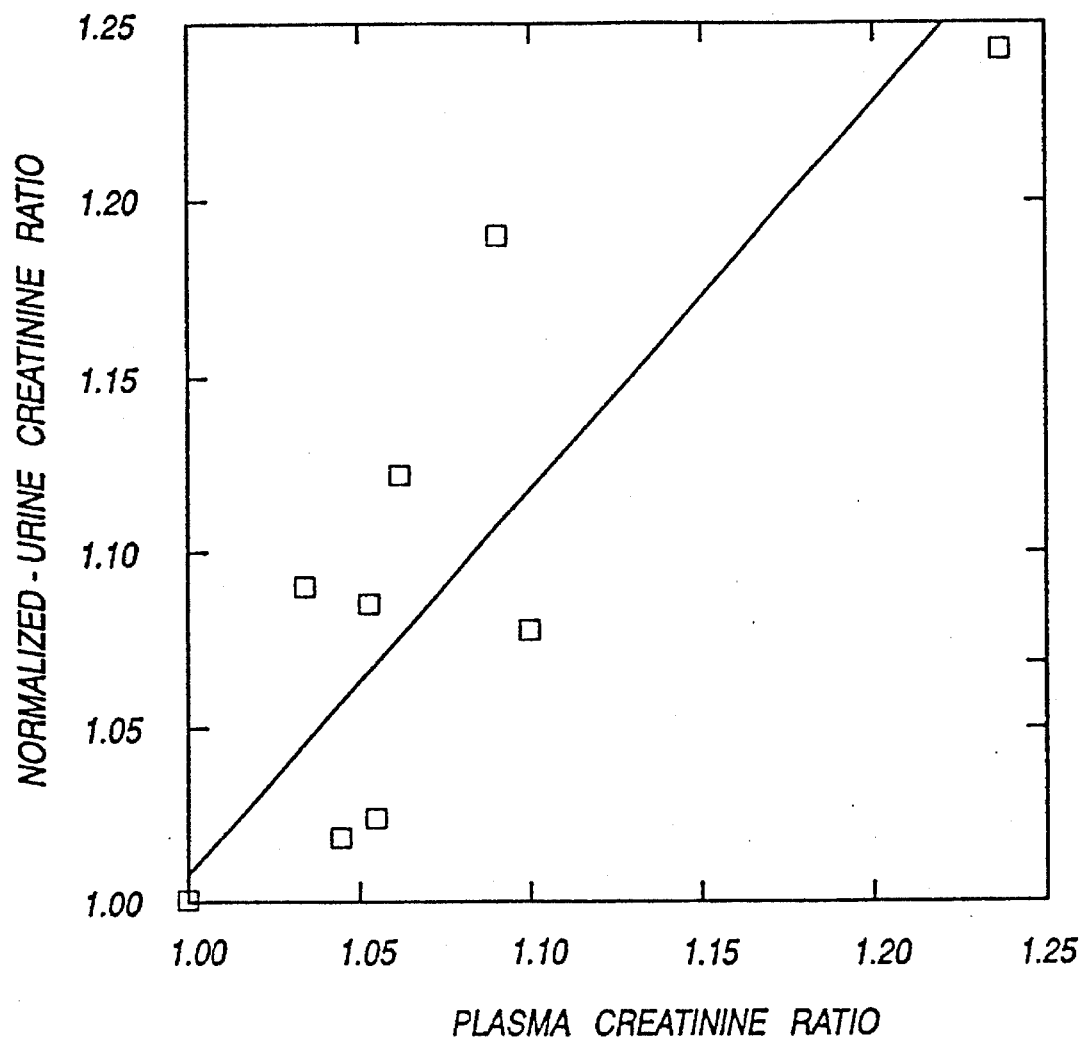
FIG. 3 is an empirically derived graph of normalized-urine creatinine ratio versus plasma creatinine ratio showing their linear relationship.

The possible effects of this daily variation in plasma creatinine concentration was explored. Simultaneous AM and PM measurements of plasma and urine creatinine concentrations were made in several subjects. Taking the lowest plasma creatinine concentration as the plasma reference and the corresponding specific gravity normalized urine creatinine concentration as the urine reference, ratios of the form $X/XR_{Ref}$ were calculated. FIG. 3 displays data for nine subjects plotted as plasma creatinine ratio versus specific gravity normalized urine creatinine ratio. Inspection of this curve indicates that specific gravity normalized urine creatinine concentration is essentially linearly related to plasma creatinine concentration. Thus, small daily variations in plasma creatinine concentrations are accurately related in the urine such that creatinine clearance remains virtually constant.

Day-to-day variability for specific gravity normalized urine creatinine concentration were followed in a patient cohort using once or twice a week urine testing. Analysis of this data demonstrated a mean CV of 15.5 % with a standard deviation of 4.4 %. Based upon these results, the slight amounts of biological variability seen for plasma creatinine concentration is not expected to significantly effect the utilization of this new method.

Standard vs. Proposed Estimates for Creatinine Clearance

Comparative data demonstrating acceptable agreement between conventional clinical estimates of creatinine clearance and those of the present invention was generated. Each subject was asked to measure and record the amount and time of each urine void. Specific gravity and urine and plasma creatinine concentrations were measured for each subject. Using this data, creatinine clearances were calculated using Equation (10). Shown in Table B is detailed collection data for a single subject with a plasma creatinine concentration of approximately 1.29 mg/dl. Shown in Table C is summary data for six subjects.

Using Osmolality Measurement In Lieu of Specific Gravity Measurement in Calculations It has been noted that specific mathematical relationships exist between the rate of urine formation (ml/min) and the concentration of creatinine in the urine. A relationship also exists between these variables and urine specific gravity. Generally, the relationships between SGF and v/v' apply to persons with normal renal function. However one situation exists in which the SGF, especially when measured by refractometry or hydrometer, is not directly related to v/v', thus creating inaccuracies in the relationships heretofore described. This situation occurs whenever the urine contains a significant amount of protein and/or glucose. Occasionally this can also occur whenever urinary cleared, radiopaque dyes are used for diagnostic purposes. Each of these compounds can affect the refractive index or drag coefficients for a spinning hydrometer. In situations such as these, the presence of the abnormal components results in the specific gravity value being artificially elevated. For example, protein in the urine, which is mainly albumin, causes the specific gravity to increase by about 0.003 units for every 1000 mg of protein/100 ml urine. The presence on glucose results in an increase of about 0.004 units for every 1000 mg of glucose/100 ml urine. If the presence of these influencing compounds is not considered, the specific gravity utilized in the correlation is inaccurate. This inaccuracy is readily apparent because the v/v' from the calculated SGF will fall outside of the expected range, alerting the clinician to a possible unusual situation. It will appear that the urine specific gravity is too high for the amount of urine produced. In this scenario, additional urine tests can be done to quantify the amounts of protein, glucose and radiopaque dyes. Once these figures are obtained, corrections can be applied to the calculations. For example, another urine sample can be collected after the radiopaque dye is out of the urine and numerical corrections to the refractometer or hydrometer specific gravity values can be made for protein and/or glucose. The corrected specific gravity is determined by subtraction so as to remove the effect of the abnormal urine components. Once these corrections are made, the normally expected relationships between SGF and v/v' may be noted.

However, in lieu of using SGF as a measure of urine concentrating ability, specific gravity being the mass of a unit volume of solution/mass of a unit volume of pure solvent, urine osmolality factor (hereinafter UOF) can also

TABLE B

Creatinine Clearance Comparison of Conventional and Proposed Methods

| Sample | Spec Grav | Act Uri Cr conc, u (mg/dl) | Nor Uri Cr conc, nu (mg/dl) | Uri Vol (ml/min) | Std. Cr Clear (ml/min)[a] | Calc. Cr Clear (ml/min)[a] |
|---|---|---|---|---|---|---|
| 1 | 1.020 | 144 | 319 | **** | **** | 108.0 |
| 2 | 1.022 | 167 | 315 | 0.83 | 106.6 | 106.5 |
| 3 | 1.024 | 219 | 352 | 0.60 | 101.1 | 119.2 |
| 4 | 1.015 | 69 | 237 | 1.17 | 62.1 | 80.1 |
| 5 | 1.009 | 40 | 266 | 2.33 | 71.7 | 90.3 |
| 6 | 1.015 | 110 | 377 | 0.98 | 82.9 | 127.7 |
| 7 | 1.019 | 117 | 282 | 1.05 | 94.5 | 95.3 |
| 8 | 1.024 | 180 | 267 | 0.70 | 96.9 | 97.9 |
| 9 | 1.025 | 240 | 289 | 0.54 | 99.7 | 97.8 |
| 10 | 1.022 | 143 | 269 | 0.94 | 103.4 | 91.2 |
| 11 | 1.015 | 64 | 219 | 2.03 | 99.9 | 74.1 |
| Mean | | 135.7 | 290.2 | | 91.9 | 99.0 |
| SD | **** | 63.7 | 47.3 | **** | 14.8 | 16.6 |
| CV (%) | | 44.6 | 16.8 | | 16.1 | 16.8 |

TABLE C

Summary Creatinine Clearance Data

| Subject | No. Urine Samples | Std. Cr Clearance (ml/min)[a] | | Calc. Cr Clearance (ml/min)[a] | |
|---|---|---|---|---|---|
| A | 5 | 87.0 | (SD 6.9) | 96.7 | (SD 7.4) |
| B | 5 | 91.2 | (SD 4.4) | 86.9 | (SD 10.1) |
| C | 7 | 111.0 | (SD 11.6) | 105.3 | (SD 11.4) |
| D | 7 | 92.0 | (SD 11.1) | 81.5 | (SD 8.4) |
| E | 7 | 89.9 | (SD 8.7) | 84.3 | (SD 12.0) |
| F | 11 | 91.9 | (SD 14.8) | 99.0 | (SD 16.6) | be used. Osmolality is the number of osmotic particles per unit volume of pure solvent. A common relationship exists in scientific literature relating urine osmolality to urine specific gravity. For instance, urine osmolality, measured in mOSM, is equal to 37500(SG-1.000). The urine osmolality factor (UOF) may be defined as the ratio of the urine osmolality at a specific gravity of 1.030, to the urine osmolality equivalent at the actual urine specific gravity as hereinafter shown. Using this equation, the following numerical relationships may be generated for protein/glucose free urines.

EXAMPLES

|  | Measured Specific Gravity | Calculated Specific Gravity Factor | Measured Osmolality | Calculated Urine Osmolality Factor |
|---|---|---|---|---|
| sample 1 | SG 1.003 | SGF 10 | Osm 112.5 | UOF 10 |
| sample 2 | SG 1.015 | SGF 2 | Osm 562 | UOF 2 |
| sample 3 | SG 1.030 | SGF 1 | Osm 1125 | UOF 1 |

It is therefore evident from this data that SGF and UOF values are equivalent and either one may be used in the application of this invention.

Refinement of Creatinine Clearance Equations

Independent data was gathered from 96 patients being followed in a renal disease clinic. Data available from these patients included 24 hour urine volumes, urine specific gravity, urine creatinine concentration, serum creatinine concentration, creatinine clearances measured from 24 hour collections, presence of protein and glucose in urine, urine osmolality, patient sex, age, lean body weight, total body weight, height and diagnosis.

Figure 4:
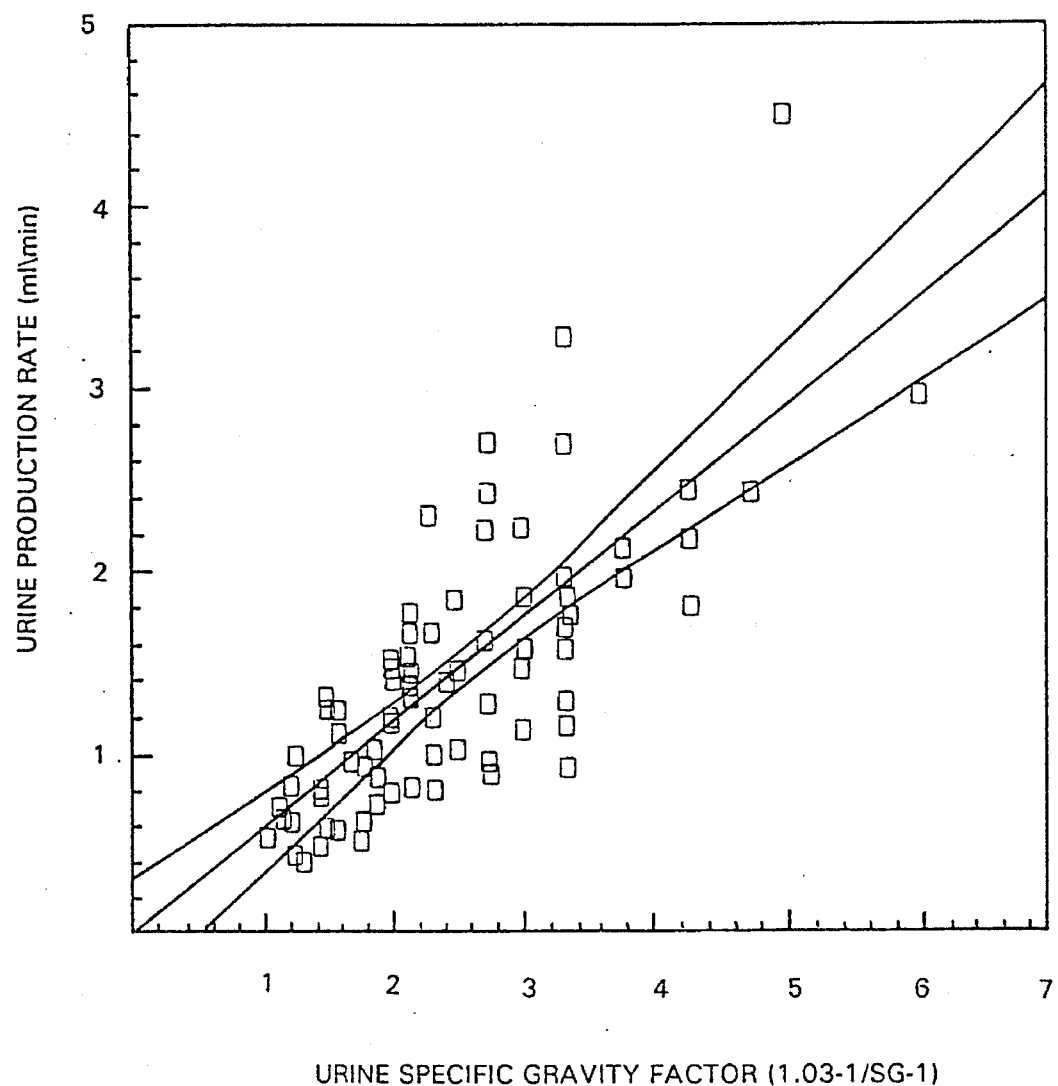
FIG. 4 is an empirically derived graph of urine production rate versus urine specific gravity factor (SGF) using independent data and showing their linear relationship.
Figure 5:
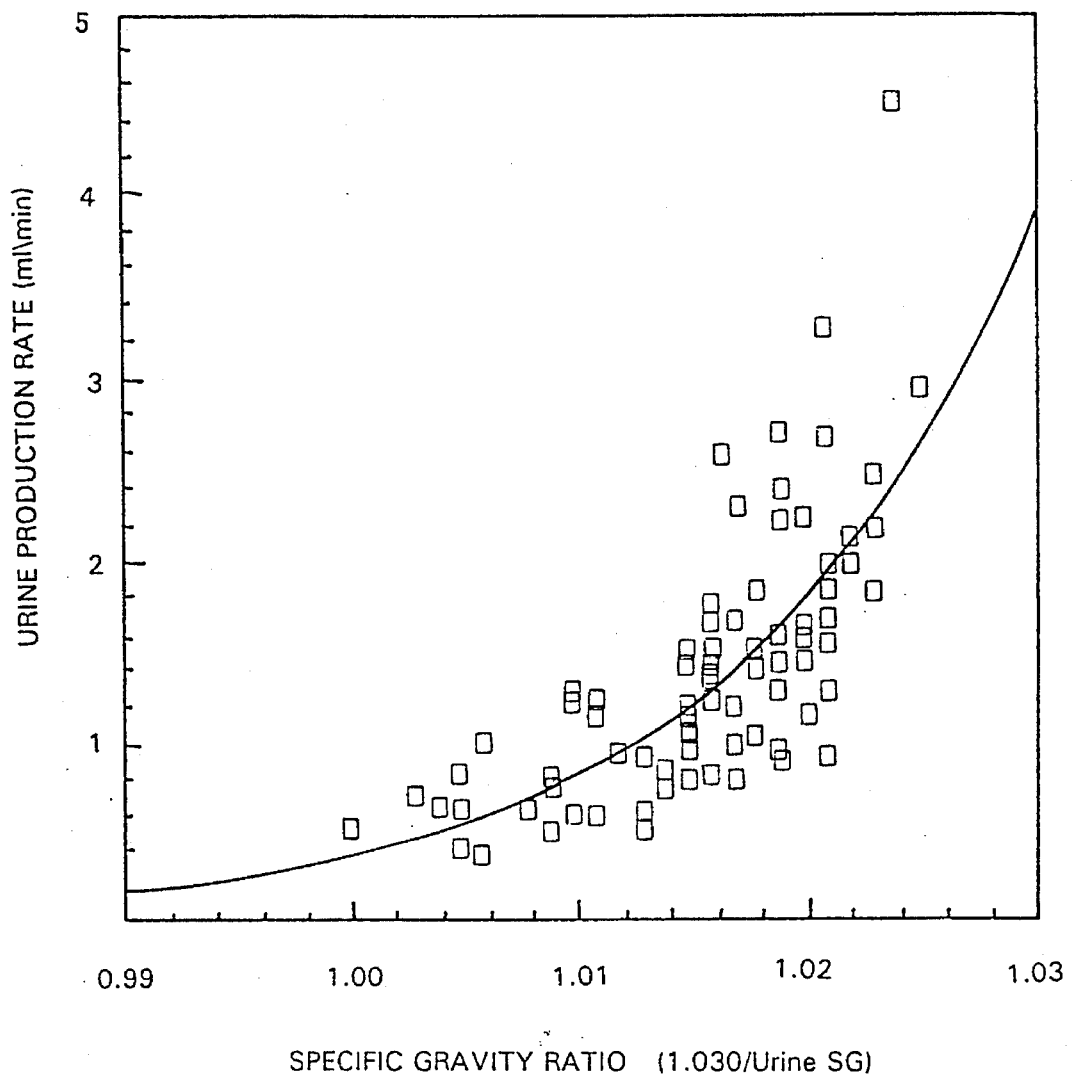
FIG. 5 is an empirically derived graph of urine production rate versus specific gravity ratio (1.030/Urine SG).

The independent data was first plotted by urine volume production rate (ml/min) versus various mathematical formulations of urine specific gravity as illustrated in FIGS. 4 and 5. Although several methods exist for plotting specific gravity or its equivalent, osmolality, on the x-axis, ie, SG ratio=1.030/SG, SGF or even SG, the SGF and UOF relationship are preferable.

Figure 6:
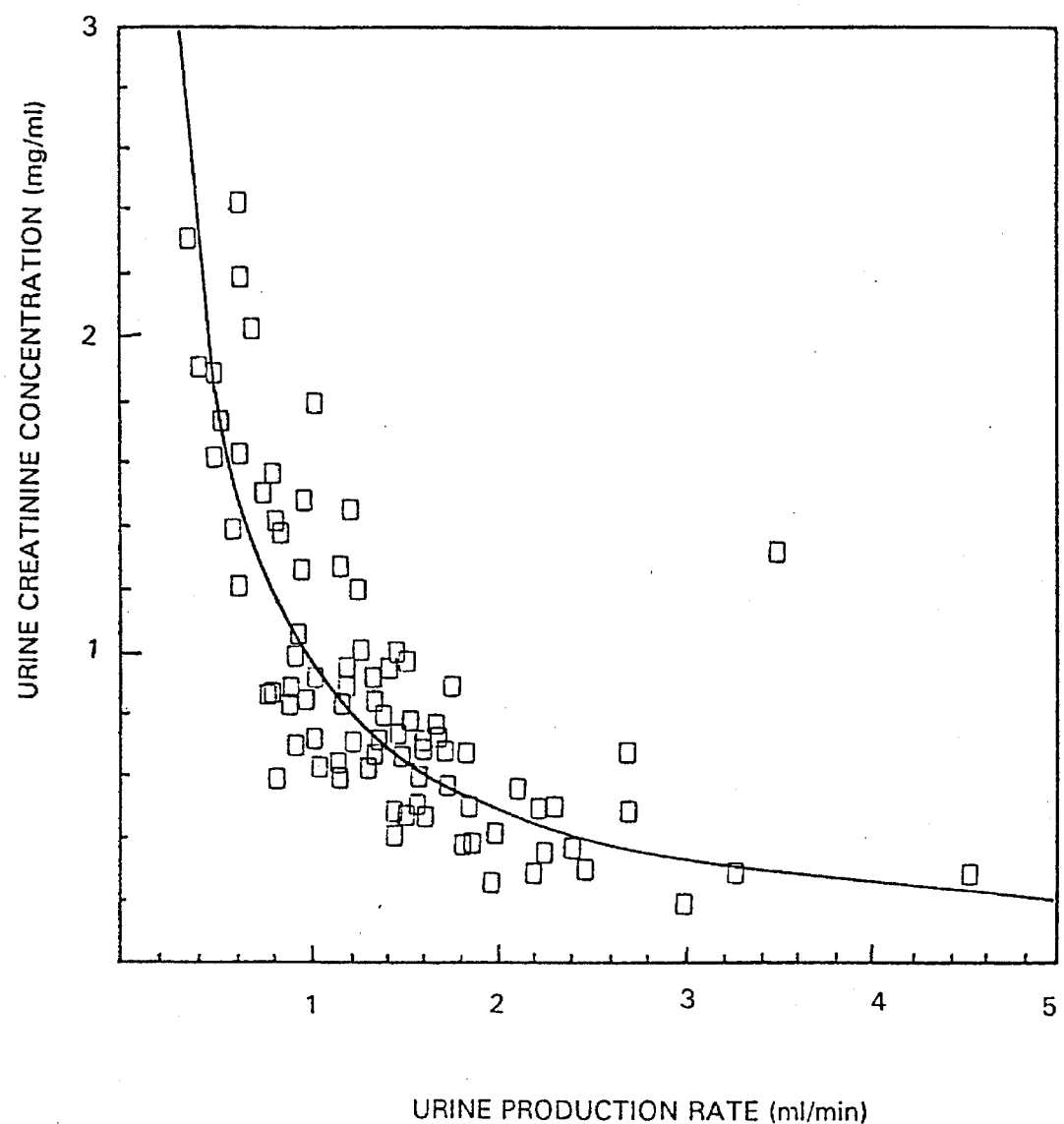
FIG. 6 is an empirically derived graph of urine creatinine concentration versus urine production rate showing the inverse relationship between urine creatinine and urine volume rate, forming a hyperbola.

Demonstrating in greater detail the inverse relationship between urine creatinine and urine volume rate, urine creatinine concentration was plotted against urine production rate revealing a hyperbola in FIG. 6.

Figure 7:
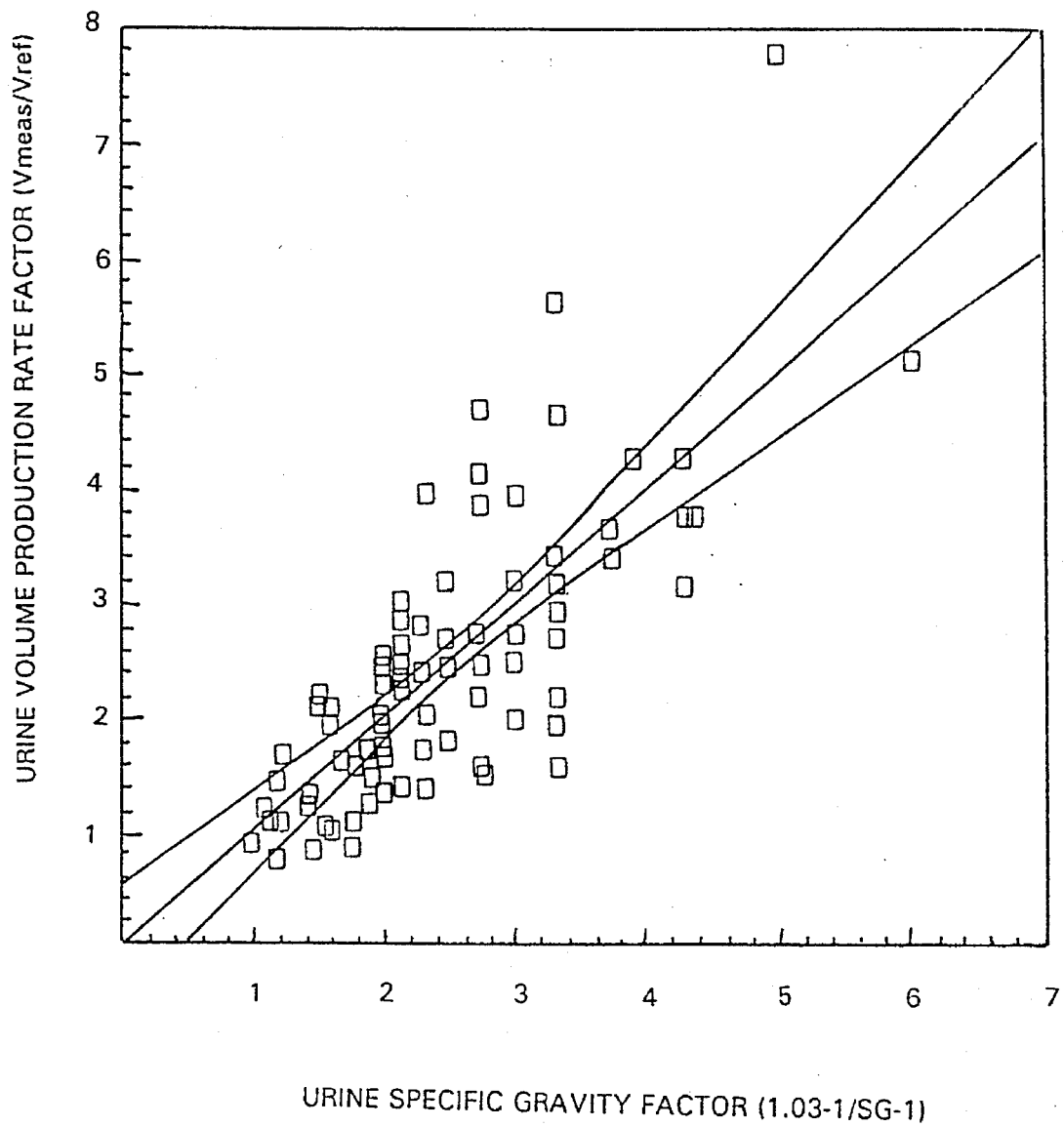
FIG. 7 is an empirically derived graph of urine volume production rate factor versus urine specific gravity factor, showing a slope of one and a zero intercept and demonstrating their linear relationship.

FIG. 7 plots the ratio v/v' using v' equal to 0.58 ml/min against SGF. Plotting this data gives a slope of one and a zero intercept. Data gathered from normal subjects supports this same conclusion.

These functions differ from functions described earlier in that v' is now equal to 0.58 and v is now equal to SGF·v' as compared to previous formulations where v was equal to (2.43·SGF-1.43)·v', where v' equals 0.44. The refined equation may be expressed generally as follows:

$$cl=v'\cdot u\cdot SGF/p \qquad (11)$$

where cl is the creatinine clearance, v' is the urine volume production rate for persons with reasonably normal renal functions, u is the measured urine creatinine concentration, SGF is the calculated specific gravity factor, and p is the measured plasma creatinine concentration.

While the earlier described functions helped to create reliable indicators this latter function using 0.58 is preferred since it is based upon greater amounts of SG versus urine volume and urine concentration data than the earlier formulation and therefore offers a more reliable predictor. With the exception of very dilute urines, and low specific gravity, the results are similar since SGF function and v' are inversely related.

Alternatively, instead of using SGF, UOF may be used as an indicator of urine concentrating ability. In this instance the following equation may be used:

$$cl=v'\cdot u\cdot UOF/p \qquad (12)$$

where cl is the creatinine clearance, v' is the urine volume production rate for persons with reasonably normal renal functions, u is the measured urine creatinine concentration, UOF is the calculated urine osmolality factor, and p is the measured plasma creatinine concentration.

Figure 8:
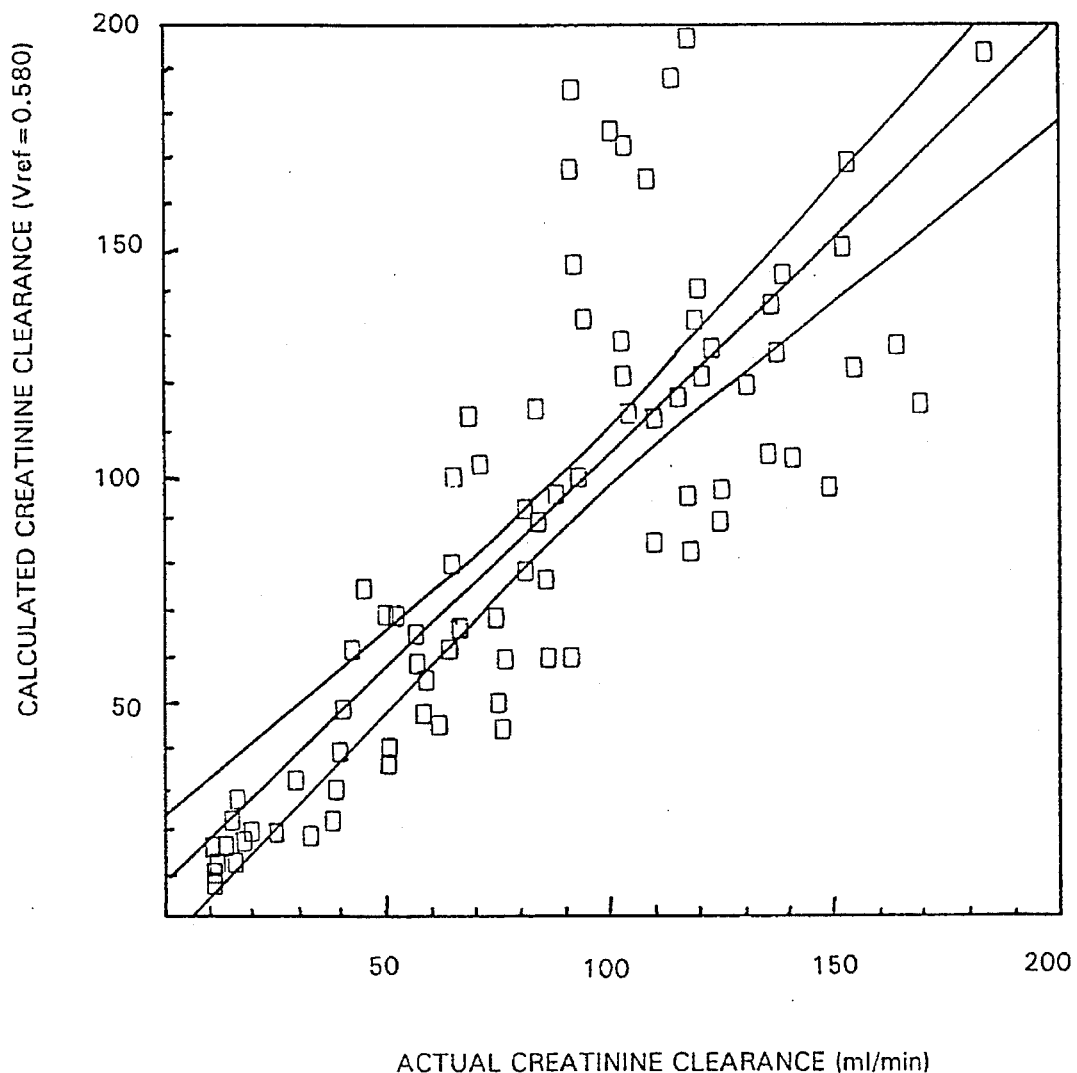
FIG. 8 is an empirically derived graph showing calculated versus actual creatinine clearances for the patients of an independent study illustrating a generally linear relationship.

FIG. 8 shows calculated versus actual creatinine clearances for the patients of the independent study illustrating a generally linear graph and the usefulness of this latter relationship.

SUMMARY

It is thus seen that a method is now provided for monitoring creatinine clearance in ambulatory and hospitalized patients using spot urine samples rather than timed urine sample collection. The method utilizes readily obtainable urine creatinine concentrations from evaluation of patient urine samples to determine specific gravity normalized urine creatinine concentrations. Alternatively, creatinine clearance values are determined using urine osmolality factor values instead of specific gravity factor values in order to avoid inaccuracies caused by artificially inflated specific gravity values which require adjustment to compensate. Osmolality factor values are preferable when it is known that patients have a history of elevated protein or glucose levels in their urine specimens. All can be compared to historical patient data to follow trends in renal GFR. The invention is clinically practical without high laboratory cost or the need to collect timed urine samples or use exogenous markers.

While these new methods have been described in detail with particular references to the preferred embodiments thereof, it should be understood that many modifications, additions and deletions may be made thereto without departure from the spirit and scope of the inventive method as set forth in the following claims.

I claim:

1. A method of determining creatinine clearance for use in detecting and monitoring renal dysfunction comprising the steps of:

(a) obtaining spot samples of urine and blood from a person;

(b) measuring specific gravity and creatinine concentration of the urine sample;

(c) calculating the specific gravity factor;

(d) measuring creatinine concentration of plasma of the blood sample; and (e) calculating creatinine clearance as a function of the calculated urine specific gravity factor, the measured urine creatinine concentration and the measured plasma creatinine concentration.

2. The method of claim 1, wherein step (e) creatinine clearance is calculated in accordance with the equation $$cl=v'\cdot u\cdot SGF/p$$

where cl is the creatinine clearance, v' is the urine volume production rate for persons with reasonably normal renal functions, u is the measured urine creatinine concentration, SGF is the calculated specific gravity factor, and p is the measured plasma creatinine concentration.

3. A method of determining creatinine clearance for detecting and monitoring renal dysfunction comprising the steps of:
   (a) obtaining spot samples of urine and blood from a person;
   (b) measuring osmolality and creatinine concentration of the urine sample;
   (c) calculating urine osmality factor;
   (d) measuring creatinine concentration of the plasma of the blood sample; and
   (e) calculating creatinine clearance as a function of the calculated urine osmolality factor, the measured urine creatinine concentration and the measured plasma creatinine concentration.

4. The method of claim 3 wherein step (e) the creatinine clearance is calculated in accordance with the equation $$cl = v' \cdot u \cdot UOF/p$$

where cl is the creatinine clearance, v' is the urine volume production rate for persons with reasonably normal renal functions, u is the measured urine creatinine concentration, UOF is the calculated urine osmolality factor, and p is the measured plasma creatinine concentration.

5. A method of determining creatinine clearance for detecting and monitoring renal dysfunction comprising the steps of:
   (a) obtaining spot samples of urine and blood from a person;
   (b) measuring the osmolality and creatinine concentration of the urine sample;
   (c) calculating the urine osmolality factor;
   (d) measuring the creatinine concentration of serum of the blood sample; and
   (e) calculating creatinine clearance as a function of the calculated urine osmolality factor, the measured urine creatinine concentration and the measured serum creatinine concentration.

6. The method of claim 5 wherein step (e) the creatinine clearance is calculated in accordance with the equation $$cl = v' \cdot u \cdot UOF/p$$

where cl is the creatinine clearance, v' is the urine volume production rate for persons with reasonably normal renal functions, u is the measured urine creatinine concentration, UOF is the urine osmolality factor, and p is the measured serum creatinine concentration.

* * * * *

UNITED STATES PATENT AND TRADEMARK OFFICE
CERTIFICATE OF CORRECTION

PATENT NO. : 5,602,038
DATED : February 11, 1997
INVENTOR(S) : Michael Kell

It is certified that error appears in the above-indentified patent and that said Letters Patent is hereby corrected as shown below:

Col. 3, line 50: 1.004 to 1.035

Signed and Sealed this

Fifth Day of August, 1997

Attest:

BRUCE LEHMAN

Attesting Officer

Commissioner of Patents and Trademarks